(12) United States Patent
Best et al.

(10) Patent No.: US 11,006,944 B2
(45) Date of Patent: May 18, 2021

(54) SURGICAL DEVICE AND METHODS OF DELIVERING IMPLANTS

(71) Applicant: Arthrex, Inc., Naples, FL (US)

(72) Inventors: Joshua Joseph Best, Naples, FL (US); Kenneth T. Helenbolt, Naples, FL (US); Andrew Osika, Naples, FL (US); Timothy J. Haughton, Newton, MA (US); Marshall Dean, Wakefield, MA (US); Omar Bermudez, Brookline, MA (US); Charles William Sears, Boxford, MA (US); Timothy N. Johnson, Freeport, ME (US)

(73) Assignee: Arthrex, Inc., Naples, FL (US)

( * ) Notice: Subject to any disclaimer, the term of this patent is extended or adjusted under 35 U.S.C. 154(b) by 182 days.

(21) Appl. No.: 15/643,520

(22) Filed: Jul. 7, 2017

(65) Prior Publication Data

US 2019/0008503 A1 Jan. 10, 2019

(51) Int. Cl.
*A61B 17/04* (2006.01)
*A61B 17/00* (2006.01)

(52) U.S. Cl.
CPC ...... *A61B 17/0401* (2013.01); *A61B 2017/00367* (2013.01); *A61B 2017/00407* (2013.01);
(Continued)

(58) Field of Classification Search
CPC ...... A61B 17/04–0401; A61B 17/0469; A61B 2017/0403–0464; A61B 2017/047–048;
(Continued)

(56) References Cited

U.S. PATENT DOCUMENTS

| | | | | |
|---|---|---|---|---|
| 5,810,848 A | * | 9/1998 | Hayhurst | ............... A61B 17/04 606/139 |
| 5,928,252 A | * | 7/1999 | Steadman | .......... A61B 17/0482 606/139 |

(Continued)

FOREIGN PATENT DOCUMENTS

| | | |
|---|---|---|
| WO | WO 2006/086275 A2 | 8/2006 |
| WO | WO 2016/068896 A1 | 5/2016 |

OTHER PUBLICATIONS

Fromm M.D., Stuart E., Black Hills Orthopedic and Spine Center, Rapid City, South Dakota. RapidLoc Meniscal Repair System, Mitek Products of Ethicon, Inc. a Johnson & Johnson Company. Scanned, Apr. 10, 2017.

(Continued)

*Primary Examiner* — Sarah A Simpson
(74) *Attorney, Agent, or Firm* — Blank Rome LLP

(57) ABSTRACT

This disclosure relates to a surgical device configured to deliver implants and a method of repairing damaged tissue, such as meniscus tears. One exemplary surgical device includes a cannula and a pusher moveable within the cannula to deploy a plurality of implants. Movement of the pusher in the distal direction deploys a distal-most implant and moves any additional implants distally within the cannula. Thus, multiple implants can be loaded into the cannula and deployed using one pusher. The disclosed arrangement is easy to use and has fewer component parts compared to prior devices, which in turn increases the ease of manufacture and reduces cost.

23 Claims, 6 Drawing Sheets

(52) U.S. Cl.
CPC ......... *A61B 2017/0409* (2013.01); *A61B 2017/0417* (2013.01); *A61B 2017/0419* (2013.01); *A61B 2017/0445* (2013.01); *A61B 2017/0464* (2013.01)

(58) Field of Classification Search
CPC .......... A61B 17/401; A61B 2017/0409; A61B 2017/00367
See application file for complete search history.

(56) References Cited

U.S. PATENT DOCUMENTS

| | | | |
|---|---|---|---|
| 5,972,027 A | 10/1999 | Johnson | |
| 6,488,691 B1* | 12/2002 | Carroll | A61B 17/0401 606/148 |
| 8,828,054 B2 | 9/2014 | Caborn et al. | |
| 8,961,538 B2 | 2/2015 | Koogle, Jr. et al. | |
| 2006/0190042 A1 | 8/2006 | Stone et al. | |
| 2008/0140092 A1* | 6/2008 | Stone | A61B 17/04 606/144 |
| 2008/0140093 A1 | 6/2008 | Stone et al. | |
| 2013/0035698 A1* | 2/2013 | Stone | A61B 17/0401 606/139 |
| 2015/0142052 A1 | 5/2015 | Koogle, Jr. et al. | |
| 2018/0055506 A1* | 3/2018 | Weber | A61B 17/0401 |

OTHER PUBLICATIONS

Smith & Nephew, Q-Fix All-Suture Implants. ArthroCare Corporation, Austin, TX. Retrieved from: http://www.smith-nephew.com/global/assets/pdf/products/surgical/sportsmedicine/qfix_brochure_a1141b.pdf. P/N A1141 Rev. B Jan. 2015. Copyright 2015.

Ochiai, M.D., Derekl Nirschl Orthopedic Center, Arliginton, VA. Omnispan Meniscal Repair, utilizing the Chia Percpasser Suture Passer. DePuy, Mitek Inc. a Johnson & Johnson Company. P/N 901087 Rev. A 1/10. Retrieved from: http://synthes.vo.llnwd.net/o16/LLNWMB8/US%20Mobile/Synthes%20North%20America/Product%20Support%20Materials/Technique%20Guides/CA5723%20OMNISPAN%20Utilizing%20CHIA%20Surgical%20Technique%20PN%20901087-FINAL.pdf. Copyright 2010.

Lawhorn, M.D., Keith. MaxFire, Marxmen Meniscal Repair Device. Biomet Sports Medicine. http://www.biomet.com/wps/wcm/connect/internet/f11b55bb-c910-4cb9-a7b4-a7f93d98ac73/BMET0562.0-GBL-MaxFireMarXmenMeniscalRepairSurgTech.pdf?MOD=AJPERES&CONVERT_TO=url&CACHEID=f11b55bb-c910-4cb9-a7b4-a7f93d98ac73. Copyright 2014.

Lawhorn, M.D., Keith. MaxFire Meniscal Repair Device, with Zip Loop technology. Biomet Sports Medicine. Retrieved from: http://www.biomet.com/wps/wcm/connect/internet/93a6e2ef-5565-4e30-9518-58b4b5d3405e/BSM0140.0_MaxFireMeniscalRepairDeviceSurgicalProtocol.pdf?MOD=AJPERES&CONVERT_TO=url&CACHEID=93a6e2ef-5565-4e30-95f8-58b4b5d3405e. Copyright 2008.

Brown, Jr., M.D., Charles H., and Sgaglione, M.D., Nicholas. Smith & Nephew Fast-Fix 360 Meniscal Repair System. Retrieved from: http://www.smith-nephew.com/global/assets/pdf/products/surgical/fastfix360_tg.pdf. Copyright 2010.

ConMed Linvatec. Knee Preservation System. Sequent Meniscal Repair Device. Retrieved from: http://www.conmed.com/-/media/CONMED/Documents/Literature/sequent-meniscal-repair-device-brochure-m2014363.ashx. Copyright 2014.

AS Meniscal Repair Device Technique Guide. Covidien. Retrieved from: http://www.medtronic.com/content/dam/covidien/library/us/en/product/sports-surgery/as-meniscal-repair-device-technique-guide.pdf. Copyright 2012.

Cayenne Medical. CrossFix II Meniscal Repair System, Surgical Technique Guide. Scottsdale, AZ. Retrieved from: http://cayennemedical.com/wp-content/uploads/CrossFix%C2%AE-II-Surgical-Technique-Guide.pdf.

Arthrex, SpeedCinch Meniscal Repair Surgical Technique. LT1-0119-EN_E. Retrieved from: https://d1psc3qestsa61.cloudfront.net/pdfs/gD_ncSCVi0qLMAFBS3JpWA/gD_ncSCVi0qLMAFBS3JpWA.pdf?Expires=1499371947&Signature=ejyYLT8rOK3WGOSCi18WsEYNTxfBflpablbzUWlkcOuNqXilDxyhgzQhQeTXPSXux3CvhCRqylq5IO67qoDuv845099-S3JJzEF9ZvKMxxhCE8jioKWRujSneqfStChCiEkv0VUgZ4lecqcndqkEUa9kTwa3EAQLdvmgsl~GqQDbSYrLTDD-.

* cited by examiner

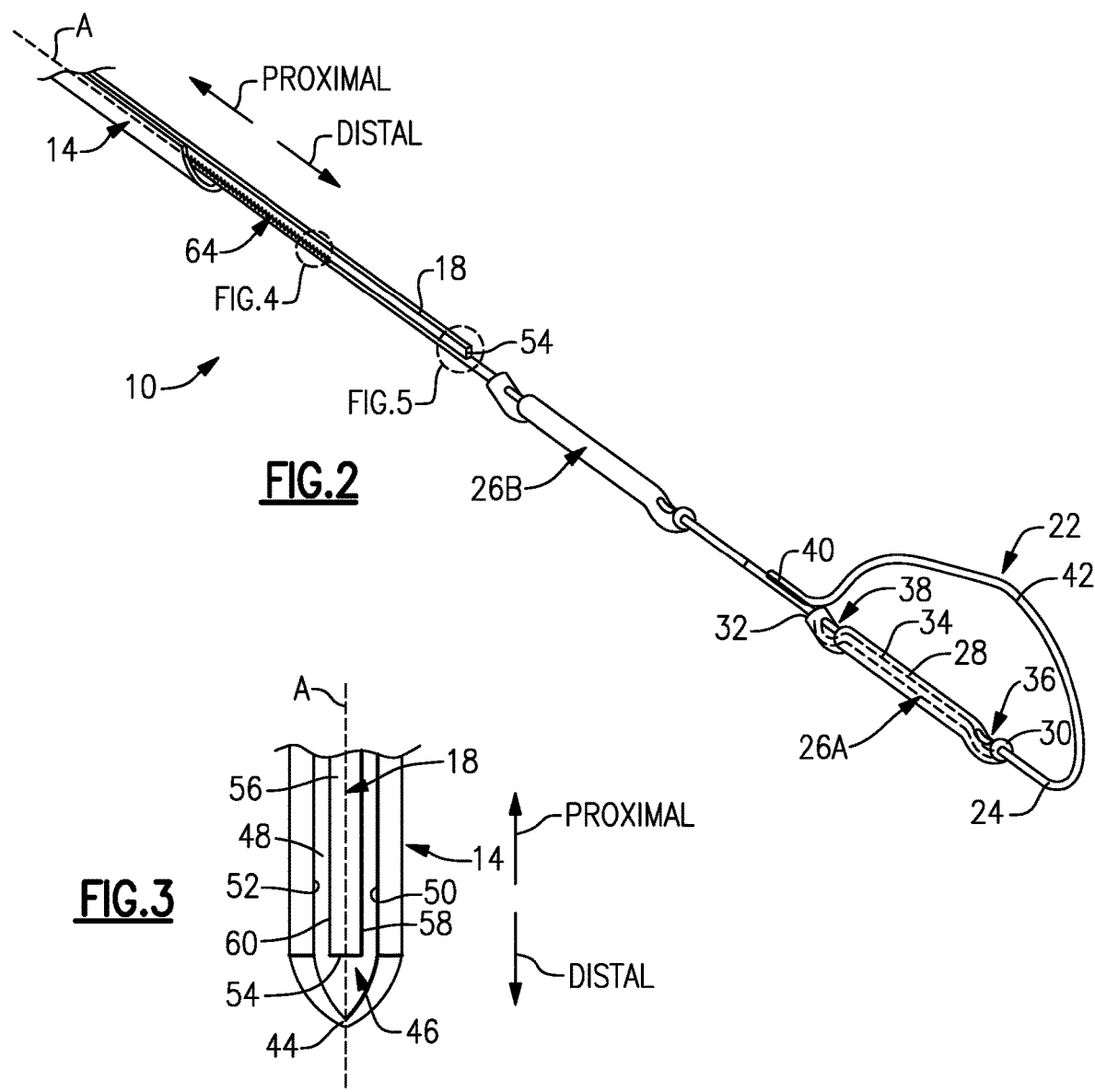
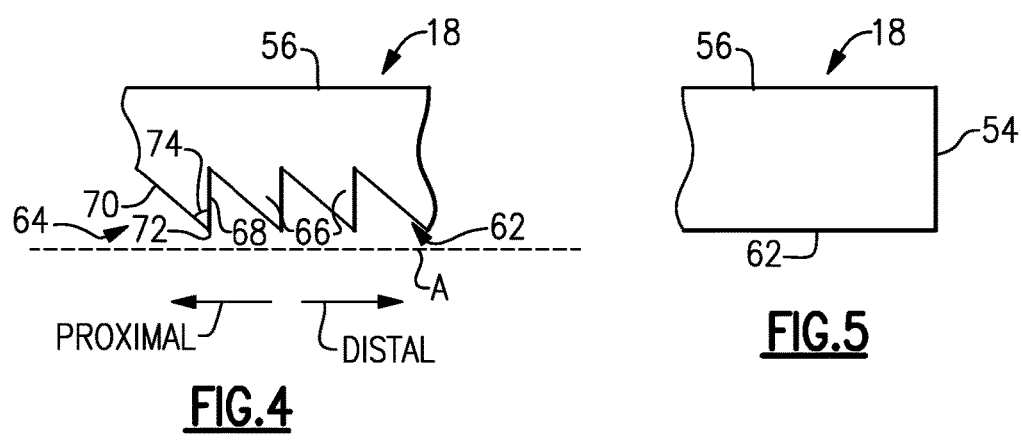

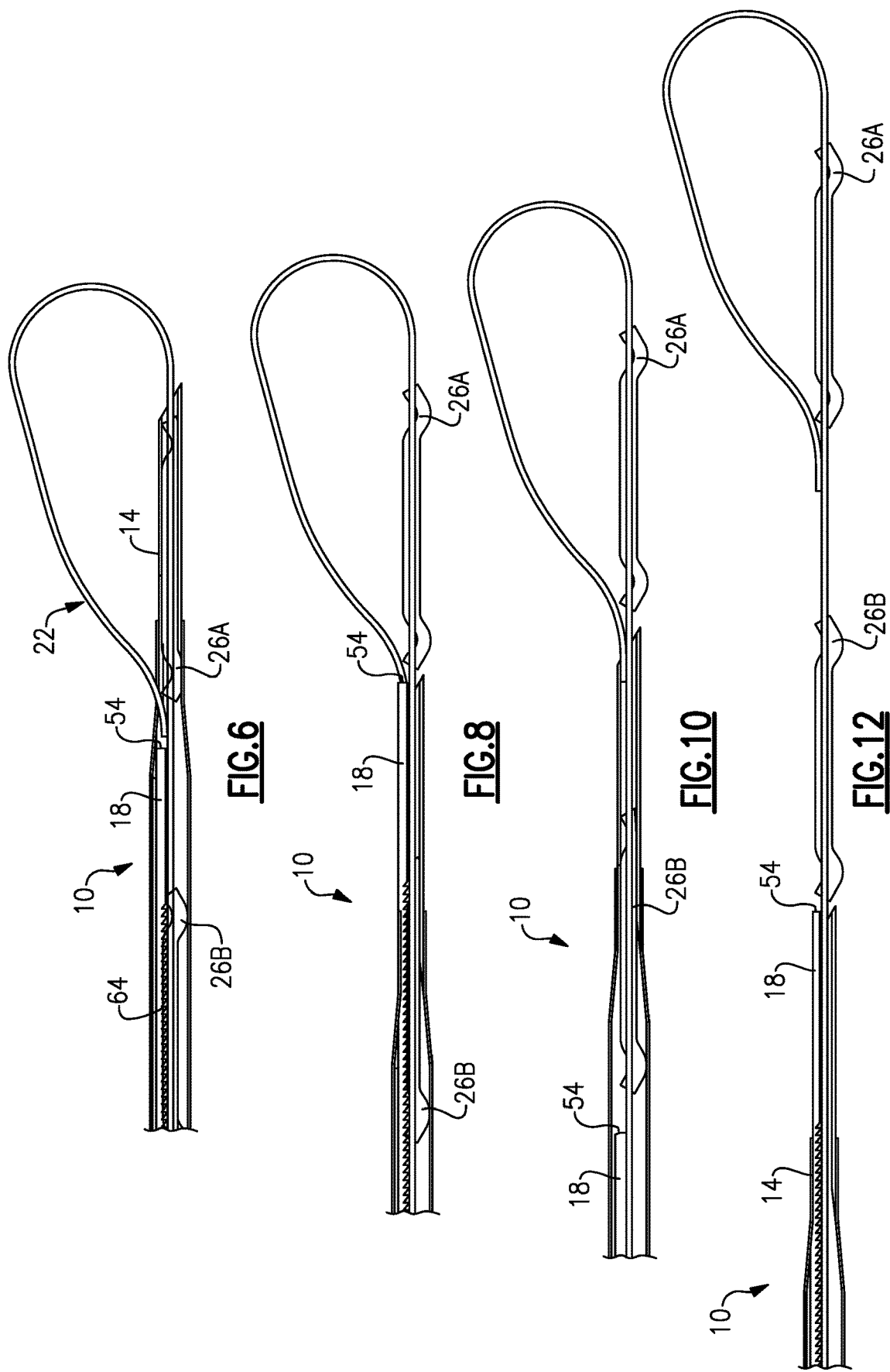

SURGICAL DEVICE AND METHODS OF DELIVERING IMPLANTS

BACKGROUND

This disclosure relates to a surgical device configured to deliver implants and a method of repairing damaged tissue.

Orthopedic procedures are often performed to repair musculoskeletal injuries, such as those sustained during sporting activities. Tears in the meniscus are known to be repaired by deploying implants on either side of the tear, cinching suture between the implants to close the tear, and allowing it to heal.

SUMMARY

This disclosure relates to a surgical device configured to deliver implants and a method of repairing damaged tissue, such as meniscus tears. One exemplary surgical device includes a cannula and a pusher moveable within the cannula to deploy a plurality of implants. Movement of a pusher deploys a distal-most implant and moves any additional implants distally within the cannula. Thus, multiple implants can be loaded into the cannula and deployed using one pusher. The disclosed arrangement is easy to use and has fewer component parts compared to prior devices, which in turn increases the ease of manufacture and reduces cost.

A surgical device according to an exemplary aspect of the present disclosure includes, inter alia, a cannula and a suture-implant construct within the cannula. The suture-implant construct includes a strand of suture and at least two implants. The first implant is in a deploy position, and the remaining implant(s) is in a standby position. For example, a surgical device includes a pusher moveable within the cannula to deploy a first implant and to move a second implant from the standby position to the deploy position.

A method according to an exemplary aspect of the present disclosure includes, inter alia, moving a pusher of a surgical device to deploy a first implant of a suture-implant construct out of a cannula and to move a second implant of the suture-implant construct distally within the cannula. The method also includes moving the pusher in a proximal direction, and moving the pusher in the distal direction again to deploy the second implant out of the cannula.

BRIEF DESCRIPTION OF THE DRAWINGS

FIG. 2 is a perspective view of the surgical device of FIG. 1 with a suture-implant construct and a pusher partially removed from the surgical device for purposes of illustration.

FIG. 3 is a top view of a distal end of the surgical device, and illustrates the arrangement between a cannula and the pusher.

FIG. 4 is a side view illustrating a shuttling rack.

FIG. 5 is a side view illustrating the distal end of the pusher.

FIG. 6 is a cross-sectional view illustrating the surgical device with the entire suture-implant construct loaded into the cannula.

FIG. 8 is a cross-sectional view illustrating the surgical device with a first implant deployed.

FIG. 10 is a cross-sectional view illustrating the surgical device with a second implant moved to a deploy position.

FIG. 12 is a cross-sectional view illustrating the surgical device with the second implant deployed.

DETAILED DESCRIPTION

Figure 1:
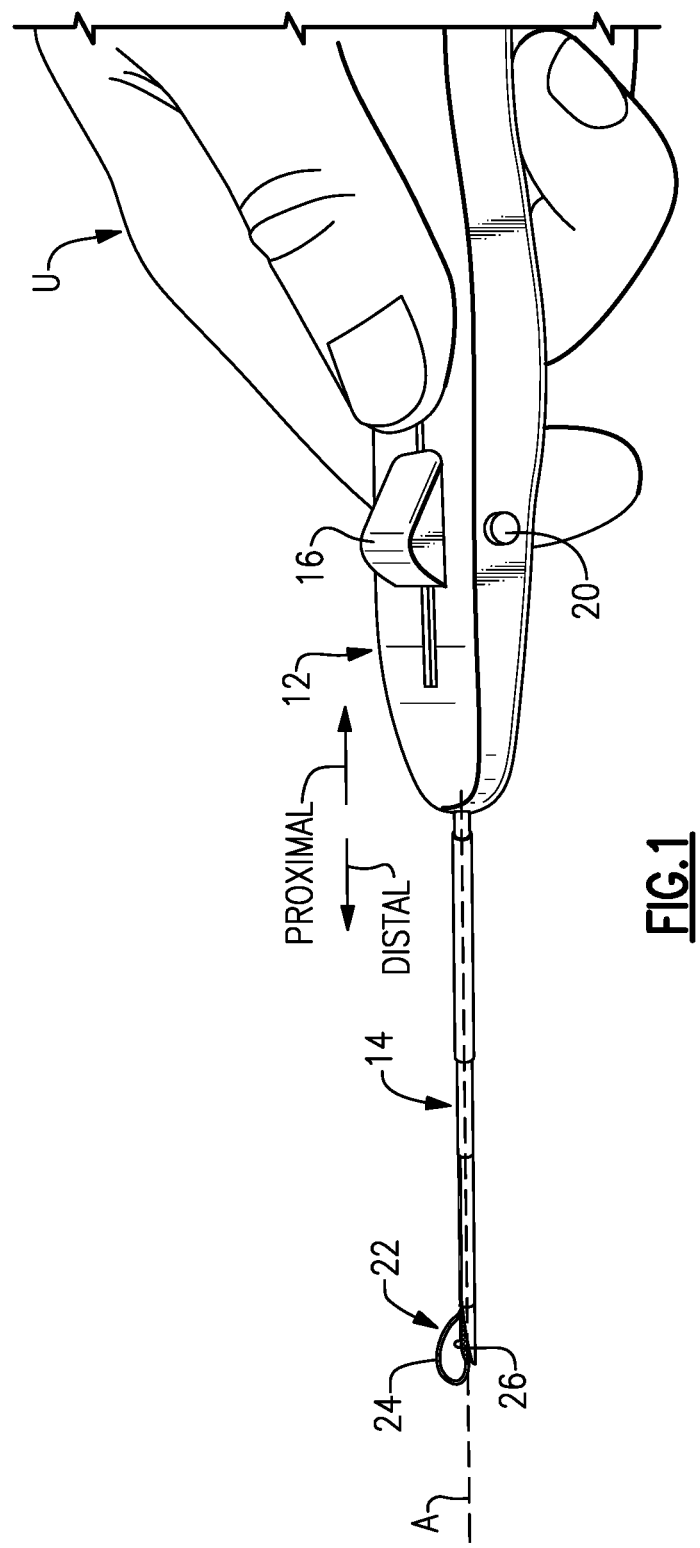
FIG. 1 illustrates an example surgical device held by a user, such as a surgeon.

This disclosure relates to a surgical device configured to deliver implants and a method of repairing damaged tissue, such as meniscus tears. An exemplary surgical device includes a cannula and a pusher moveable within the cannula to deploy a plurality of implants. Movement of the pusher deploys a distal-most implant and moves any additional implants distally within the cannula. Thus, multiple implants can be loaded into the cannula and deployed using one pusher. The disclosed arrangement is easy to use and has fewer component parts compared to prior devices, which in turn increases the ease of manufacture and reduces cost.

A surgical device according to an exemplary aspect of the present disclosure includes, inter alia, a cannula and a suture-implant construct including a strand of suture and at least two implants. The first implant is in a deploy position and the second implant is in a standby position proximal to the first implant. The surgical device further includes a pusher moveable within the cannula in a distal direction to deploy the first implant and to move the second implant from the standby position to the deploy position.

In a further embodiment of the foregoing surgical device, a pusher includes a shuttling rack in contact with the second implant when the second implant is in the standby position.

In a further embodiment of any of the foregoing surgical devices, the shuttling rack is integrated into the pusher.

In a further embodiment of any of the foregoing surgical devices, the cannula includes a slot, and the pusher is arranged within the slot.

In a further embodiment, a pusher includes an elongate shaft extending along a cannula.

In a further embodiment, a shuttling rack includes a plurality of barbs on a side of the elongate shaft.

In a further embodiment, each of the plurality of barbs has a distal face and proximal face meeting at an apex. Further, the distal face is substantially normal to a longitudinal axis of the cannula, and the proximal face is inclined at an acute angle relative to the distal faces.

In a further embodiment, a surgical device further includes a trigger configured to move in a distal direction and a proximal direction, and the trigger is mechanically coupled to the pusher such that movement of the trigger moves the pusher.

In a further embodiment, a trigger is a thumb trigger.

In a further embodiment, a trigger is biased in the proximal direction.

In a further embodiment, a surgical device includes a brake configured to be selectively activated to overcome a bias of a trigger and maintain a position of the trigger and a pusher.

In a further embodiment, implants are tubular sleeves made of a flexible material.

In a further embodiment, implants are made of a polyester suture material.

In a further embodiment, a suture-implant construct includes a third implant proximal to the second implant and a fourth implant proximal to the third implant.

A method according to an exemplary aspect of the present disclosure includes, inter alia, moving a pusher of a surgical device in a distal direction to deploy a first implant of a suture-implant construct out of a cannula and to move a second implant of the suture-implant construct distally within the cannula. The method also includes moving the pusher in a proximal direction, and moving the pusher in the distal direction again to deploy the second implant out of the cannula.

In a further embodiment, a method includes first and second implants that are implanted into a meniscus to repair a tear in the meniscus.

In a further embodiment, a method includes the pusher comprising a shuttling rack having barbs inclined such that the shuttling rack only moves the second implant in the distal direction.

In a further embodiment, a method includes moving a pusher in a distal direction to apply an input force to a trigger to overcome bias in the proximal direction.

In a further embodiment, a method includes braking a pusher to hold the position of the pusher after moving the pusher in the distal direction and before the pusher moves back to the proximal direction under the bias.

FIG. 1 illustrates an example surgical device 10 according to the present disclosure. The surgical device 10 includes a handle 12 and a cannula 14 projecting distally (the "distal" direction is labeled in various figures for reference) from the handle 12 along a longitudinal axis A. The handle 12 includes a trigger 16, which in this example is a thumb trigger. The trigger 16 is moveable in the distal and proximal directions (the "proximal" direction is labeled in various figures reference) to move a pusher 18 (FIG. 2), which itself is moveable within the cannula 14 in the distal and proximal directions.

In one example, the handle 12 includes a spring or other biasing element configured to bias the trigger 16 in the proximal direction. In order to move the trigger 16 in the distal direction, a user U (i.e., a surgeon) uses their thumb, for example, to apply a force to the trigger 16 sufficient to overcome the bias of the spring such that the trigger 16 slides distally. When the user U releases their thumb, the trigger 16 moves proximally back to a resting position under the bias of the spring or other biasing element.

The handle 12 may optionally incorporate a brake. In this example, the brake is selectively activated by depressing a button 20 disposed on an exterior surface of the handle 12. When the button 20 is depressed, the brake engages the trigger 16, or a structure associated with the trigger 16, to hold the trigger 16 in place and overcome the proximal bias of the trigger 16. This braking function is useful in some circumstances, such as when penetrating the meniscus with the cannula 14, for example.

The cannula 14 is configured to penetrate soft tissue within the body. To this end, a distal-most tip of the cannula 14 is relatively sharp and may be tapered or pointed in some examples. Further, the cannula 14 is loaded with a suture-implant construct 22 (sometimes referred to as a "suture construct"), which includes a strand of suture 24 and at least one implant 26. A user can position the cannula 14 adjacent a meniscus tear, for example, and use the trigger 16 to selectively deploy the at least one implant 26.

FIG. 2 illustrates a distal end of the surgical device 10 with the pusher 18 and suture-implant construct 22 partially removed from the cannula 14 for ease of reference. In this example, the suture-implant construct 22 includes a first implant 26A and a second implant 26B, each of which are arranged along the strand of suture 24. The first implant 26A is distal of the second implant 26B. It should be understood that while two implants 26A, 26B are illustrated, there could be additional implants. In one particular example, there are four implants arranged sequentially along the strand of suture 24.

The suture-implant construct 22 may be referred to as a "soft" construct because it is formed of soft materials such as yarns, fibers, filaments, strings, fibrils, strands, sutures, etc., or any combination of such materials. The soft materials may be synthetic or natural materials, or combinations of synthetic and natural materials, and may be biodegradable or non-biodegradable within the scope of this disclosure. In an embodiment, the suture-implant construct 22 is made exclusively of soft, suture-based materials. The soft materials confer the ability to be inserted into or through tissue (e.g., bone, ligament, tendon, cartilage, etc.) and then bunch together, collapse, expand, and/or change shape to fixate the suture-implant construct 22 relative to the tissue.

The first implant 26A includes a sheath 28 having a tubular body that extends between opposing ends 30, 32 of the sheath 28. The sheath 28 further includes a bore 34 communicating with the opposing ends 30, 32 for accommodating the strand of suture 24.

In an embodiment, the sheath 28 is a tubular sleeve made of a flexible material, such as a braided, woven, or knitted structure made of yarns, fibers, filaments, sutures, or other similar materials, or combinations of these materials. In another embodiment, the sheath 28 is constructed of polyester suture material. Other flexible materials may also be suitable for constructing the sheath 28.

The strand of suture 24 is flexible and is passed through the bore 34 of the sheath 28. The strand of suture 24 also exits and re-enters the bore 34 through a plurality of splice points 36, 38 of the sheath 28. The splice points 36, 38 are spaced from the ends 30, 32 of the sheath 28. When the first implant 26A is deployed adjacent soft tissue, tension is applied to the suture 24, which cinches the first implant 26A, anchoring it in place. While the above discussion focuses on the detail of the first implant 26A, it should be understood that the second implant 26B is arranged in the same manner.

In an embodiment, the strand of suture 24 is provided by one of the following example types of suture: FiberWire®, TigerWire®, or FiberChain® suture, which are each available from Arthrex, Inc. It should be understood, however, that any type of suture may be used, including cored or coreless sutures. In another embodiment, the strand of suture 24 is flat suture, such as FiberTape® or SutureTape® suture, which are also available from Arthrex, Inc. The strand of suture 24 may also be a monofilament suture. Further, the strand of suture 24 could include any soft, flexible strand of material, and is not limited to suture.

In this embodiment, an end 40 of the strand of suture 24 is looped over the distal-most implant of the suture-implant construct 22, which in this example is the first implant 26A. In particular, the end 40 is passed through the first implant 26A, and is bent back in the proximal direction and affixed to the strand of suture 24 at a location proximal to the first implant 26A. The end 40 may be affixed back to the strand of suture 24 by a knot or using some other fixation technique. The result is a loop 42 enclosing a portion of the first implant 26A. The loop 42 retains the first implant 26A relative to the stand of suture 24 and ensures that the first implant 26A does not slide distally off the strand of suture 24.

FIG. 3 illustrates the arrangement between the cannula 14 and the pusher 18 from a top view (i.e., a superior view). As noted above, the cannula 14 is configured to penetrate soft tissue. To this end, the cannula 14 is tapered to a sharp, pointed distal end 44 in this example. The cannula 14 further includes a tubular bore 46, which receives the suture-implant construct 22 and the pusher 18. In this example, the cannula 14 further includes a slot 48 in a superior surface thereof. The slot 48 extends parallel to the longitudinal axis A of the cannula 14. The slot 48 includes opposing side walls 50, 52 which serve to guide movement of the pusher 18 in a direction parallel to the longitudinal axis A. The slot 48 may extend along a portion of the length of the cannula 14 or alternatively may extend along the entire length of the cannula 14.

The pusher 18 is configured to deploy a distal-most implant of the suture-implant construct 22 and is also configured to move any additional implants distally within the cannula. Specifically, in the example of the first and second implants 26A, 26B, distal movement of the pusher 18 is configured to deploy the first implant 26A and to move the second implant 26B distally within the cannula 14 to a deploy position. A second distal movement of the pusher 18 will then deploy the second implant 26B.

In one example, the pusher 18 includes a rod or shaft mechanically coupled to the trigger 16. The pusher 18 is configured to move in the distal and proximal directions in response to corresponding movement of the trigger 16. The pusher 18 further includes a blunt distal end 54 configured to push an implant in the distal direction. The distal end 54 in this example is a substantially planar surface arranged normal to the longitudinal axis A. The distal end 54 could be inclined at an acute angle relative to the longitudinal axis A. The pusher 18 further includes a relatively smooth superior surface 56, and relatively smooth side surfaces 58, 60 configured to slide relative to the respective side walls 50, 52 of the slot 48. The inferior surface 62 of the pusher 18 includes a shuttling rack 64 in this example, which is configured to interact with implants to move them distally within the cannula 14.

FIG. 4 illustrates the shuttling rack 64 in greater detail. In this example, the shuttling rack 64 is integrated into the pusher 18, meaning the shuttling rack 64 and pusher 18 are a single, integrated structure. The shuttling rack 64 includes a plurality of barbs 66 projecting from the inferior surface 62 of the pusher 18. The barbs 66 each include a distal face 68 and a proximal face 70. The distal and proximal faces 68, 70 meet at an apex 72, which provides a relatively sharp point and is configured to engage an implant. In this example, the distal faces 68 are substantially normal to the distal direction and the longitudinal axis A, and the proximal faces 70 are inclined toward the proximal direction such that they project from the apex 72 at an acute angle 74 relative to the distal faces 68.

The shuttling rack 64 is configured to move implants distally when the pusher 18 moves distally, and is also configured to not move implants proximally as the pusher 18 moves proximally. Thus, during a sequence where the user U moves the trigger 16 in the distal direction and the trigger 16 moves back proximally under the bias of the spring, for example, the implants within the cannula will only move in the distal direction.

In this example, the pusher 18 does not include barbs 66 along the entirety of its length. Rather, as shown in FIG. 5, there is a section of the pusher 18 adjacent the distal end 54 where the inferior surface 62 is smooth. The inferior surface 62 may be smooth along a length corresponding to the length of the implants 26A, 26B. Alternatively, the inferior surface 62 may have barbs 66 along its entire length.

A method of using the surgical device 10 will now be described with reference to FIGS. 6-13. FIG. 6 is a cross-sectional view of the surgical device 10 and illustrates the surgical device 10 with the suture-implant construct 22 loaded into the cannula 14. In particular, each of the first and second implants 26A, 26B are positioned within the cannula 14. The first implant 26A is a distal-most implant within the cannula 14. The distal end 54 of the pusher 18 is proximal to the first implant 26A, and the shuttling rack 64 is contact with the second implant 26B.

For purposes of this disclosure, the distal-most implant within the cannula 14 is in a "deploy position" in which the implant is ready to be deployed by the pusher 18, and any remaining implants are in a "standby position." The implants in the standby position are essentially waiting to be moved to the deploy position and ultimately deployed by the pusher 18. In FIG. 6, the first implant 26A is in the deploy position and the second implant 26B is in a standby position.

Figure 7:
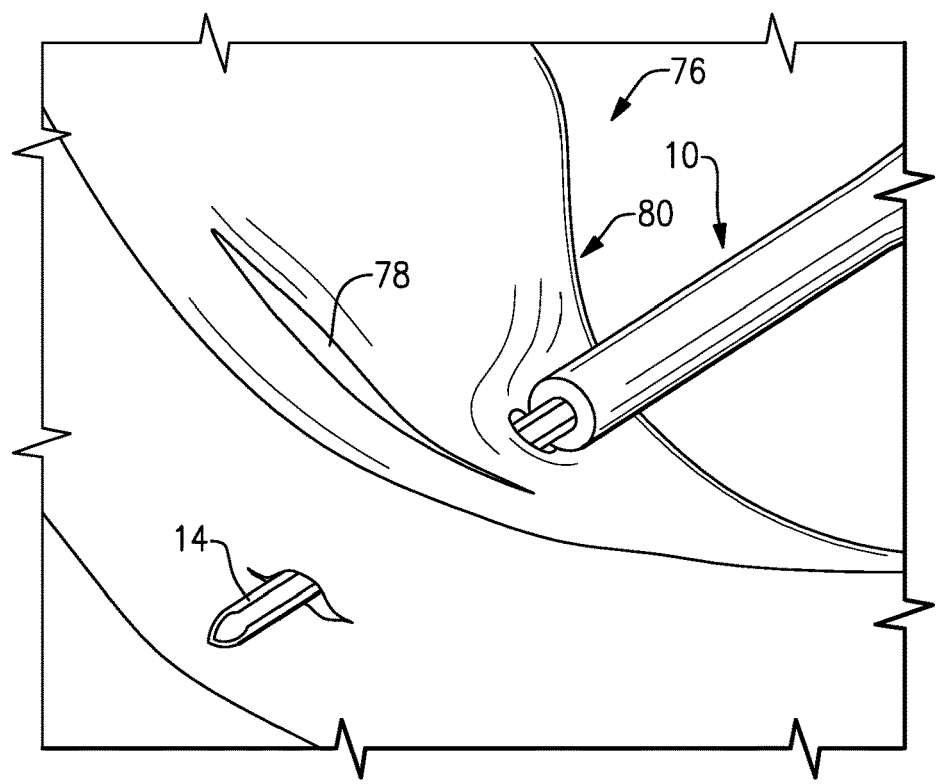
FIG. 7 is a view of the surgical device penetrating a meniscus in a first location adjacent a meniscus tear.

When in the position of FIG. 6, a user U can navigate the surgical device 10 within a joint space 76, as illustrated in FIG. 7. The joint space 76 in FIG. 7 is a joint cavity in a knee, and is specifically a cavity between a femur and a tibia. While a knee joint is illustrated, it should be understood that this disclosure extends to other joints. As illustrated in FIG. 7, there is a tear 78 in a meniscus 80. The surgical device 10 is used to deploy a plurality of implants in the area adjacent the tear 78 to close the tear 78 and allow it to heal.

Figure 9:
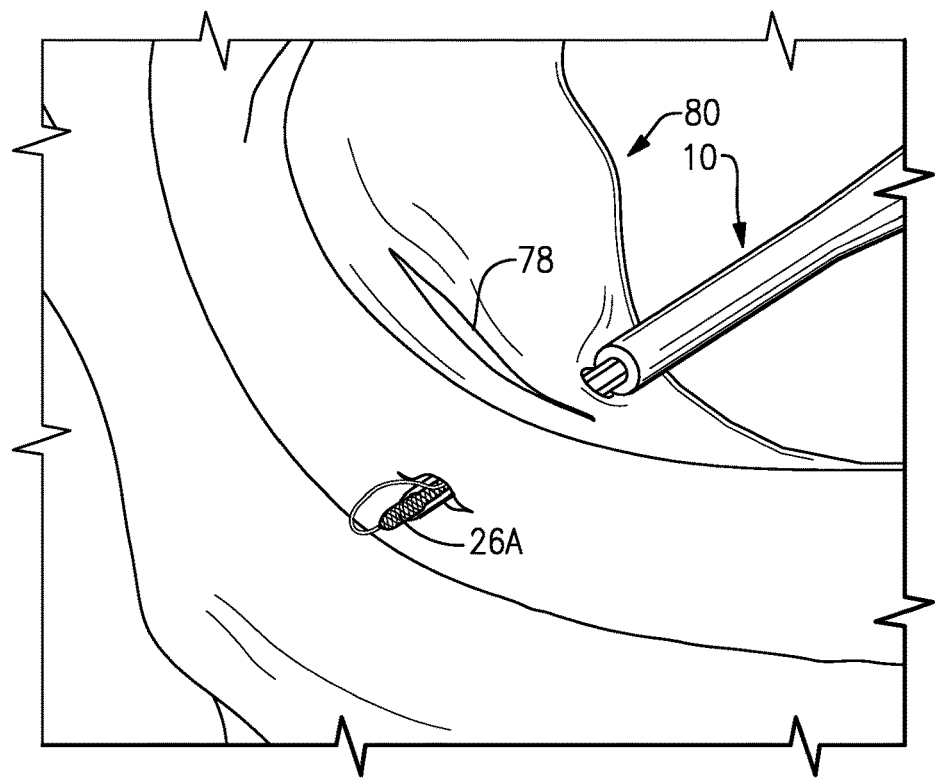
FIG. 9 is a view of the surgical device as the first implant is deployed in the first location adjacent the meniscus tear.

In FIG. 7, a user U penetrates the cannula 14 through the meniscus 80 in a first location where the first implant 26A is to be deployed. When the cannula 14 is in the first location, the user U applies an input force to the trigger 16, which moves the pusher 18 distally. In FIG. 8, movement of the pusher 18 in the distal direction has deployed the first implant 26A out of the cannula 14 and into a desired location adjacent the meniscus 80. FIG. 9 illustrates the first implant 26A as it is being deployed in the first location. Further, as shown in FIG. 8, the shuttling rack 64 has moved the second implant 26B distally within the cannula relative to its position in FIG. 6.

After the first implant 26A is deployed, the user U can remove their thumb, for example, from the trigger 16 allowing the trigger 16 and pusher 18 to move proximally to the position shown in FIG. 10. Again, proximal movement of the pusher 18 does not move the second implant 26B proximally because of the arrangement of the shuttling rack 64, discussed above. In FIG. 10, the second implant 26B is the distal-most implant in the cannula 14 and is distal to the distal end 54 of the pusher 18. Thus, the second implant 26B has moved from a standby position (e.g., FIGS. 6, 8) to the deploy position (e.g., FIG. 10).

Figure 11:
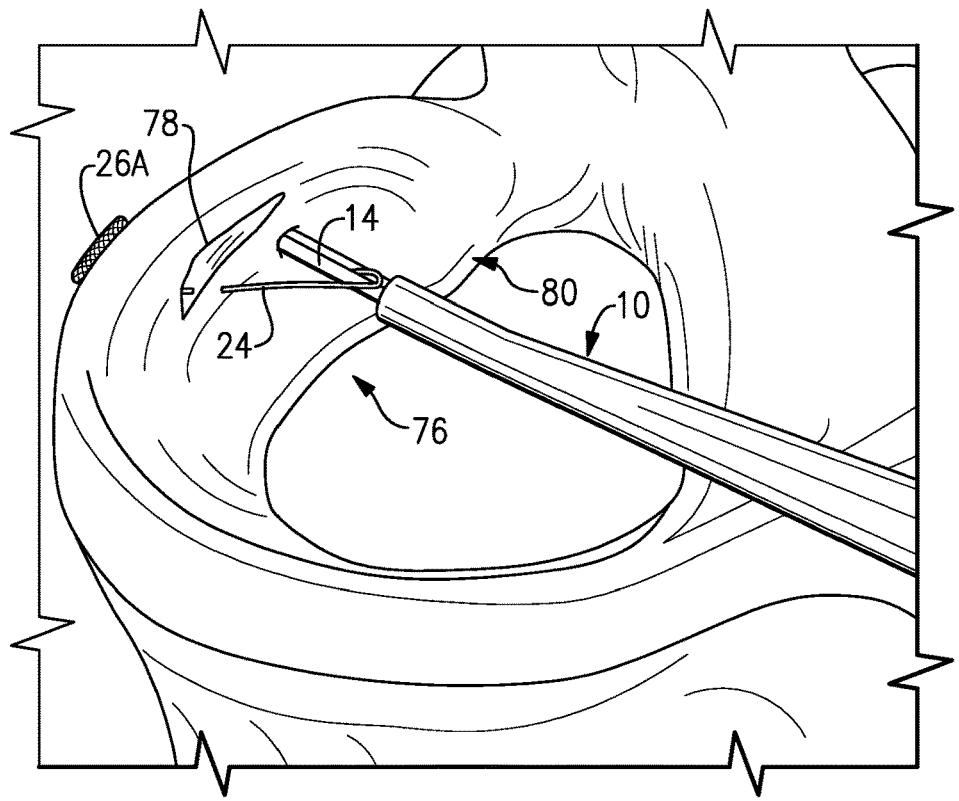
FIG. 11 is a view of the surgical device penetrating a meniscus in a second location adjacent the meniscus tear.
Figure 13:
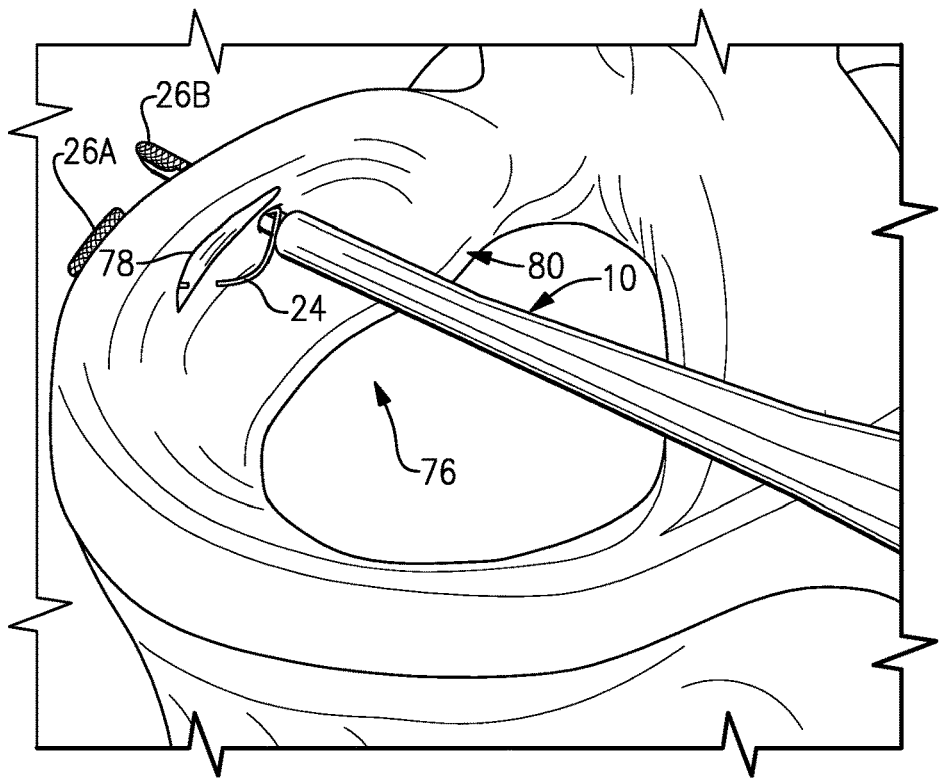
FIG. 13 is a view of the surgical device as the second implant is deployed in the second location adjacent the meniscus tear.

When in the position of FIG. 10, the user U can position the cannula 14 in a second location adjacent the tear 78, as shown in FIG. 11. The second location is spaced-apart from the first location of FIG. 7. Once in the second location, the user U can penetrate the meniscus 80 and move the trigger 16 in the distal direction, which moves the pusher 18 in the distal direction, and deploys the second implant 26B, as illustrated in FIG. 12. FIG. 13 illustrates the second implant 26B as it is being deployed in the second location.

Figure 14:
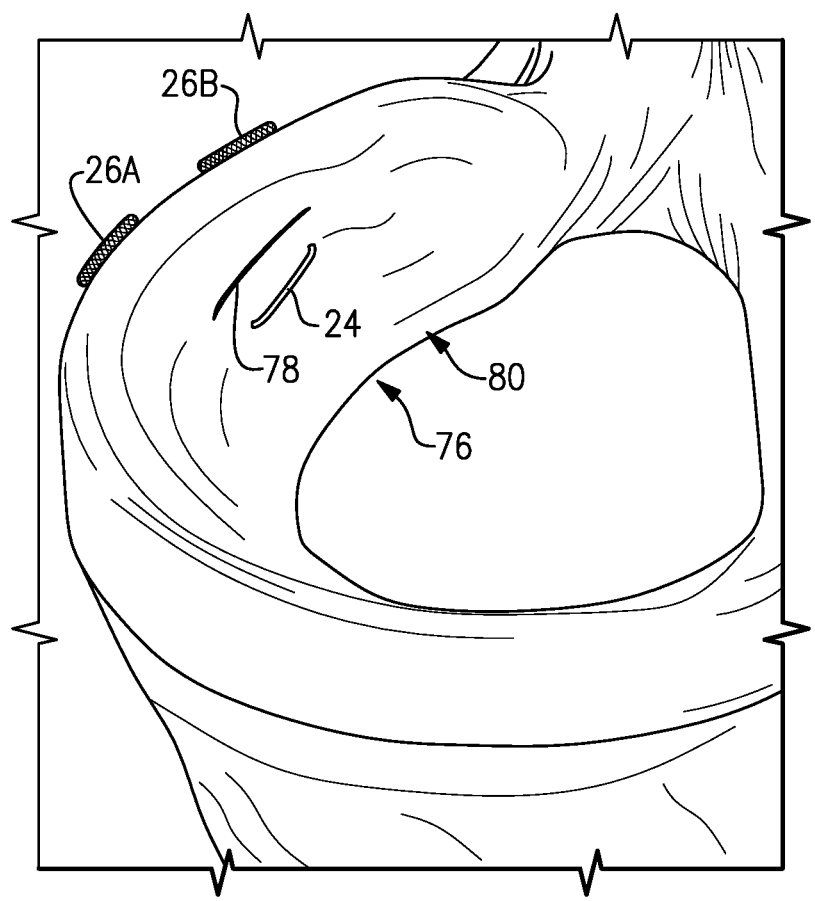
FIG. 14 is a view of a closed meniscus tear.

Once the first and second implants 26A, 26B are deployed, the suture 24 can then be tensioned, knotted, and trimmed. Doing so closes the tear 78, as generally shown in FIG. 14. For larger tears, for example, additional implants can be used. In that case, the trigger 16 can be activated additional times to deploy each additional implant.

It should be understood that terms such as "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A surgical device, comprising:
   a cannula;
   a suture-implant construct comprising a single suture and at least two implants arranged along the single suture, wherein a first implant is in a deploy position and a second implant is in a standby position proximal to the first implant, each of the first and second implants being a tubular sleeve formed of flexible material, each sleeve having an inner bore, and the single suture being threaded through the inner bore of the sleeve of at least the first implant; and
   a pusher moveable within the cannula in a distal direction to deploy the first implant and moveable in a proximal direction to move the second implant from the standby position to the deploy position, and the pusher having a distal most end that is proximal to the first implant both prior to and after deployment of the first implant.

2. The surgical device as recited in claim 1, wherein the pusher includes a shuttling rack in direct contact with the second implant when the second implant is in the standby position.

3. The surgical device as recited in claim 2, the shuttling rack is integrated into the pusher.

4. The surgical device as recited in claim 2, wherein the shuttling rack includes a plurality of barbs.

5. The surgical device as recited in claim 4, wherein each of the plurality of barbs has a distal face and proximal face meeting at an apex, and wherein each distal face is substantially normal to a longitudinal axis of the cannula, and each proximal face is inclined at an acute angle relative to each distal face.

6. The surgical device as recited in claim 1, wherein the cannula includes a slot, and wherein the pusher is arranged within the slot.

7. The surgical device as recited in claim 1, wherein the pusher includes an elongate shaft extending along the cannula and the distal most end of the pusher is a planar face configured to push the first implant in the distal direction.

8. The surgical device as recited in claim 1, further comprising a trigger mechanically coupled to the pusher such that movement of the trigger moves the pusher in both the distal direction and the proximal direction.

9. The surgical device as recited in claim 8, wherein the trigger is a thumb trigger.

10. The surgical device as recited in claim 8, wherein the trigger is biased in the proximal direction.

11. The surgical device as recited in claim 8, further comprising a brake configured to be selectively activated to overcome a bias of the trigger and maintain a position of the trigger and the pusher.

12. The surgical device as recited in claim 1, wherein the flexible material is a polyester suture material.

13. The surgical device as recited in claim 1, wherein the single suture threads through splice points in the first and second implants.

14. The surgical device as recited in claim 13, wherein the splice points of each of the first and second implants are spaced from opposite ends of the respective sleeve thereof.

15. The surgical device as recited in claim 1, wherein the single suture has a loop configured to enclose a portion of the first implant.

16. The surgical device as recited in claim 1, wherein the single suture threads through the inner bore of the sleeve of the second implant.

17. A surgical device, comprising:
    a cannula;
    a suture-implant construct comprising a flexible strand and at least two implants wherein a first implant is in a deploy position, and a second implant is in a standby position proximal to the first implant, each of the first and second implants being a tubular sleeve formed of flexible material, each sleeve having an inner bore, and the flexible strand being threaded through the inner bore of the sleeve of at least the first implant, wherein a portion of the flexible strand is distal to the first implant; and
    a pusher configured to move within the cannula in a distal direction when deploying the first implant and in proximal direction when moving the second implant from the standby position to the deploy position, and the pusher having a distal most end that is proximal to the first implant both prior to and after deployment of the first implant.

18. The surgical device as recited in claim 17, wherein the flexible strand is a single suture and the first and second implants are arranged along the single suture.

19. The surgical device as recited in claim 17, wherein the flexible strand is threaded through splice points in the first and second implants.

20. The surgical device as recited in claim 17, wherein the pusher includes a shuttling rack in contact with the second implant when the second implant is in the standby position.

21. The surgical device as recited in claim 17, further comprising a trigger configured to move in the distal and proximal directions, wherein the trigger is mechanically coupled to the pusher such that movement of the trigger moves the pusher.

22. The surgical device as recited in claim 17, wherein the distal most end of the pusher is a planar surface configured to push the first implant in the distal direction.

23. A surgical device, comprising:
    a cannula;
    a suture-implant construct comprising a single suture and at least two implants arranged along the single suture, wherein a first implant is in a deploy position and a second implant is in a standby position proximal to the first implant, each of the first and second implants being a tubular sleeve formed of flexible material, each sleeve having an inner bore, and the single suture being threaded through the inner bore of the sleeve of at least the first implant; and a pusher moveable within the cannula in a distal direction to deploy the first implant and moveable in a proximal direction to move the second implant from the standby position to the deploy position, the pusher having a distal most end that is proximal to the first implant, and the pusher including a shuttling rack that is in direct contact with the second implant when the second implant is in the standby position, and the shuttling rack including a plurality of barbs.

\* \* \* \* \*